(12) United States Patent
Typpo

(10) Patent No.: US 6,995,372 B2
(45) Date of Patent: Feb. 7, 2006

(54) NUCLEAR GAUGE FOR MEASURING A CHARACTERISTIC OF A SHEET MATERIAL WITH SHEET POSITION AND ALIGNMENT COMPENSATION

(75) Inventor: Pekka M. Typpo, Cupertino, CA (US)

(73) Assignee: Voith Paper Patent GmbH, Heidenheim (DE)

( * ) Notice: Subject to any disclaimer, the term of this patent is extended or adjusted under 35 U.S.C. 154(b) by 235 days.

(21) Appl. No.: 10/365,339

(22) Filed: Feb. 12, 2003

(65) Prior Publication Data

US 2004/0155196 A1  Aug. 12, 2004

(51) Int. Cl.
    *G01N 21/86*  (2006.01)
(52) U.S. Cl. .................................... 250/358.1
(58) Field of Classification Search ............... 250/308, 250/359.1, 360.1, 358.1
    See application file for complete search history.

(56) References Cited

U.S. PATENT DOCUMENTS

| | | | |
|---|---|---|---|
| 3,373,286 A | * | 3/1968 | Han ........................ 250/359.1 |
| 4,276,480 A | | 6/1981 | Watson ........................ 250/560 |
| 4,678,915 A | | 7/1987 | Dahlquist et al. ......... 250/358.1 |
| 5,010,766 A | | 4/1991 | Typpo .......................... 73/159 |
| 5,118,940 A | * | 6/1992 | Davis et al. ................ 250/308 |
| 5,233,195 A | | 8/1993 | Hellstrom et al. ........ 250/360.1 |
| 6,133,578 A | | 10/2000 | Typpo ..................... 250/497.1 |

FOREIGN PATENT DOCUMENTS

EP        000628808 A1  * 12/1994

* cited by examiner

*Primary Examiner*—Constantine Hannaher
(74) *Attorney, Agent, or Firm*—Taylor & Aust, P.C.

(57) ABSTRACT

A material sheet attribute detection system, the material sheet having a first side and a second side, the system includes a radiation source located proximate to the first side of the material sheet, the radiation source emitting radiation toward the material sheet, a radiation detection array located proximate to the second side of the material sheet, the radiation detection array producing at least one signal based on the radiation detected from the radiation source and a processor utilizing the at least one signal to determine a position of the material sheet.

29 Claims, 9 Drawing Sheets

NUCLEAR GAUGE FOR MEASURING A CHARACTERISTIC OF A SHEET MATERIAL WITH SHEET POSITION AND ALIGNMENT COMPENSATION

BACKGROUND OF THE INVENTION

1. Field of the Invention

The present invention relates to a nuclear gauge for measuring a characteristic of a sheet material, and, more particularly, to a nuclear gauge for measuring a characteristic of a moving sheet material with sheet position compensation and alignment compensation.

2. Description of the Related Art

Nuclear gauges are used for measuring thicknesses of a moving sheet material, in a non-contact manner, by detecting the amount of radiation that passes through the sheet material and/or the dispersion of the radioactive emission by the sheet material. The scattering effect that the sheet material imparts to the radiation beam is often compensated for by shaping the radiation beam in an attempt to achieve insensitivity to gap size variations and flutter of the sheet material as it moves through the gauge. Flutter compensation is typically done with collimators on both the radiation source and the radiation receiver to thereby exclude rays that are deviated by a large angle due to the influence of the sheet material. Radiation source and receiver collimation is adjusted to minimize the sensitivity of the detector to flutter of the sheet material. This method usually works over only a limited range and different measurement ranges require different geometries to compensate for flutter of the sheet material. This method of compensation results in a reduce signal to noise ratio as the detection properties are limited to compensate for the flutter of the sheet material.

Compensation of gap variations is often done by blocking the center of the radiation beam being directed to the detector with a radiation absorbing disk. This disk, which is often called an $R^2$ disk, results in decreased sensitivity to gap size variation but only over a narrow range.

What is needed in the art is a way of compensating for variations in the position of the material sheet between the radiation source and the detector of a nuclear gauge.

SUMMARY OF THE INVENTION

The present invention provides a material sheet position detector which utilizes the detected position to compensate for the effect of a variation in the position of the material sheet on the radiation scattering in a nuclear gauge.

The invention comprises, in one form thereof, a material sheet attribute detection system, the material sheet having a first side and a second side, the system includes a radiation source located proximate to the first side of the material sheet, the radiation source emitting radiation toward the material sheet, a radiation detection array located proximate to the second side of the material sheet, the radiation detection array producing at least one signal based on the radiation detected from the radiation source and a processor utilizing the at least one signal to determine a position of the material sheet.

The invention comprises, in another form thereof, a method of measuring attributes of a moving material sheet including the steps of positioning a radiation source on one side of the material sheet and a detector array on an other side of the material sheet, receiving information from the detector array and calculating a position of the material sheet between the radiation source and the detector array using the information.

An advantage of the present invention is that the nuclear gauge for measuring a characteristic of a sheet material can obtain the basis weight of the sheet material in spite of misalignment of the radiation source and the detector.

Another advantage of the nuclear gauge of the present invention is that the position of the sheet material is detected based entirely upon information received from the radiation detector.

Still another advantage is that the nuclear gauge of the present invention compensates for the position of the material sheet to then calculate the basis weight of the material sheet.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
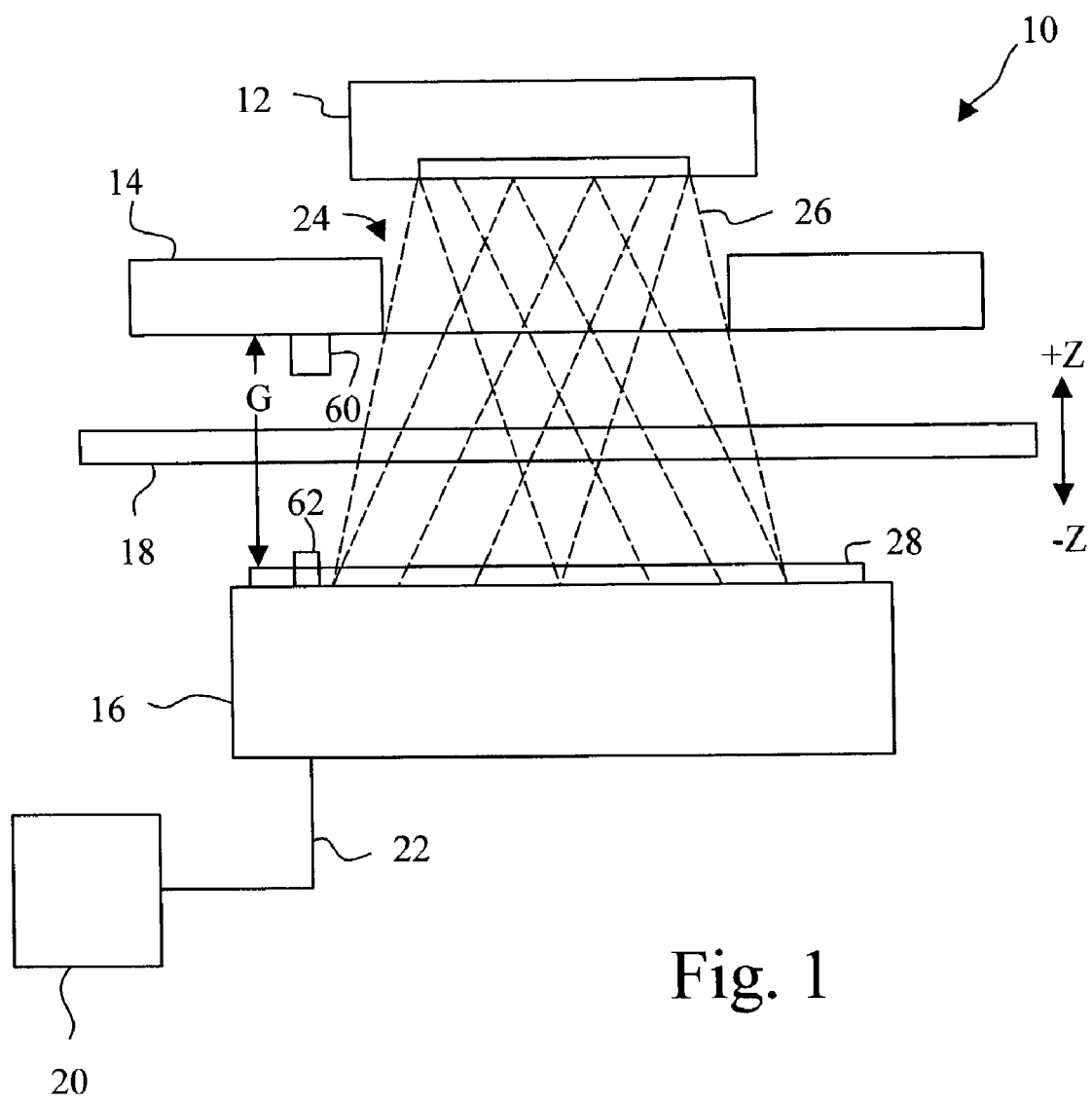
FIG. 1 is a diagrammatic side view of an embodiment of a nuclear gauge of the present invention.

Referring now to the drawings, and more particularly to FIG. 1, there is shown an embodiment of a nuclear gauge 10, also known as a material sheet attribute detection system, of the present invention including a radiation source 12, a source aperture 14, a detector array 16, a material sheet 18 and a processor 20. Radiation source 12 is a element which generates radioactive particles or radiation energy due to radioactive decay or by way of energy stimulation. Radiation source 12 may be surrounded by a radiation absorbing or reflecting material with an opening on one side to thereby mainly emit radiation from one side of radiation source 12.

Radiation source 12 may, for example, emit primarily beta particles or x-rays. Source aperture 14 includes an aperture 24 through which radiation emitted by radiation source 12 may pass through. Source aperture 14 is made from a material which will absorb or reflect radiation from radiation source 12. Aperture 24 can be closed and opened under command of processor 20 or another control mechanism.

Figure 2:
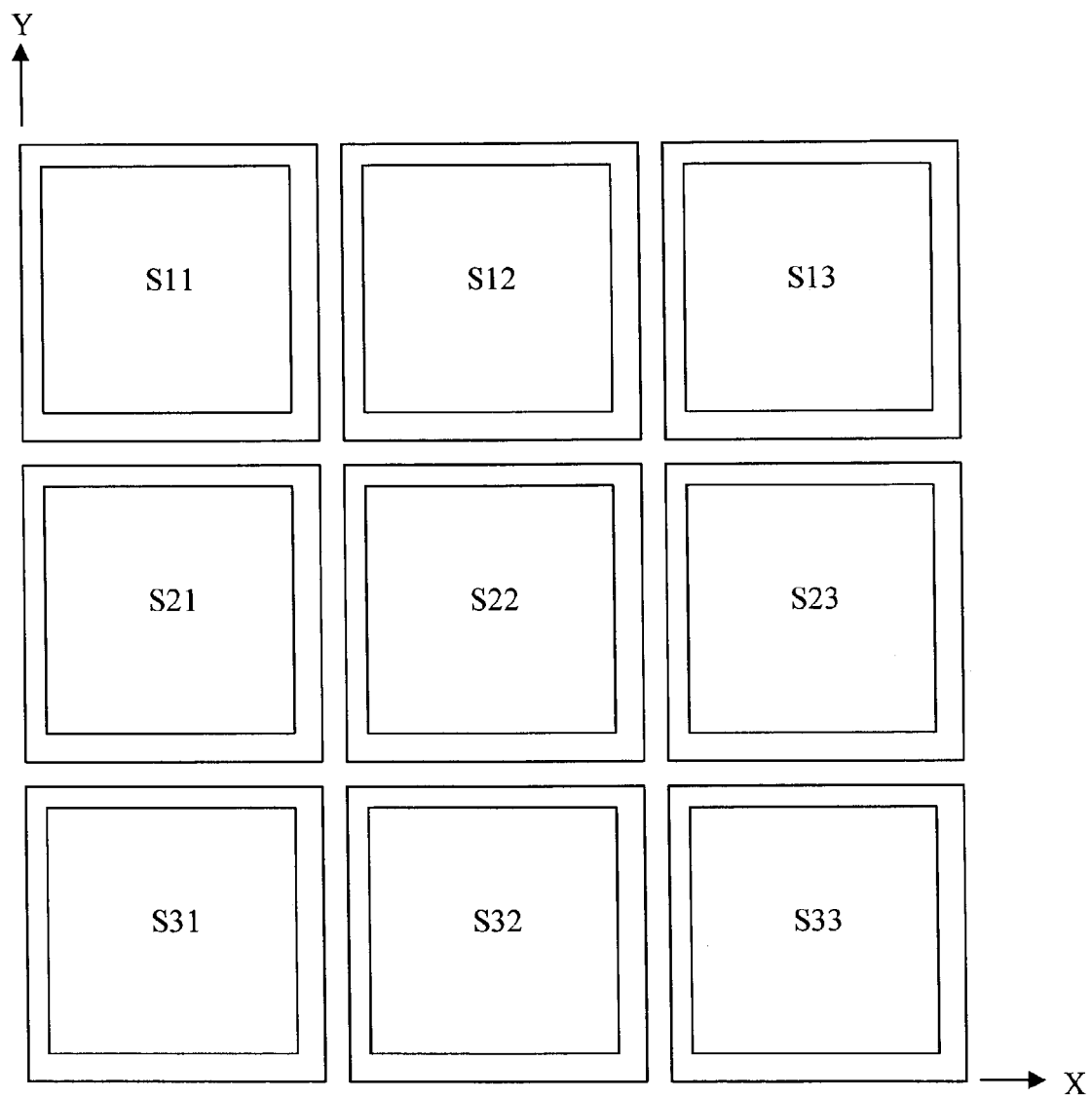
FIG. 2 is a diagrammatic view of a detector array of the nuclear gauge of FIG. 1.
Figure 3:
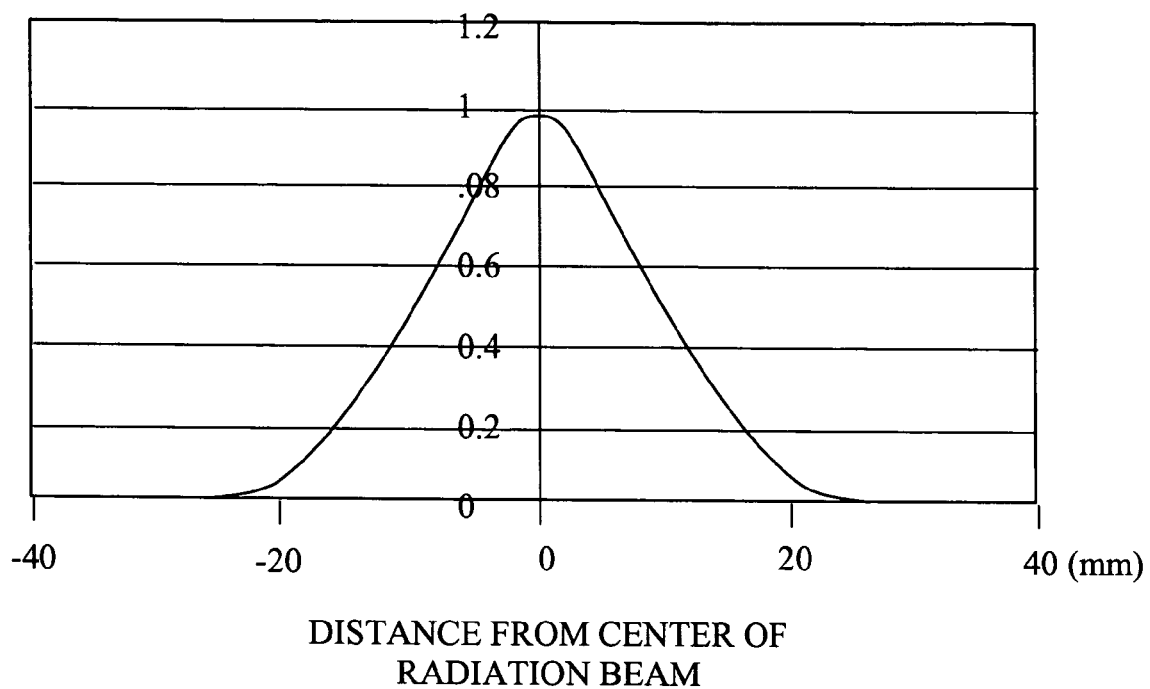
FIG. 3 is a graph indicating a radiation distribution from the radiation source of the nuclear gauge of FIG. 1.

Now, additionally referring to FIG. 2, there is shown another view of detector array 16. Detector array 16 is connected to processor 20 by way of communications link 22. Detector array 16 includes a detector window 28, and multiple individual detectors arrayed in a geometric pattern such as sensors S11, S12, S13, S21, S22, S23, S31, S32, and S33. Detector array 16 communicates to processor 20 the amount of radiation detected by each of sensors S11–S33. Detector array 16 is positioned in substantial alignment with radiation source 12 to thereby centrally locate sensor S22, so as to be substantially centered in radiation beam 26. The peak intensity of the radiation, as represented in FIG. 3, is substantially directed toward sensor S22. While a substantial alignment of radiation beam 26 is desired, the present invention determines and compensates for any misalignment. Radiation beam 26, from radiation source 12, travels through detector window 28 to arrive at detector array 16. Detector window 28 is substantially transparent to the radiation. Information or a signal from detector array 16 to processor 20 may be in the form of an analog signal or digital information, which may be in the form of a digital count that is representative of the amount of radiation detected by each of sensors S11–S33 from radiation source 12.

Material sheet 18 is suspended between detector array 16 and the combination radiation source 12 and source aperture 14. Gap G, between source aperture 14 and detector window 28, is sufficiently wide that material sheet 18 does not touch either source aperture 14 or detector window 28. Material sheet 18 is typically a moving sheet of material such as paper, cardboard or a plastic. As material sheet 18 travels in a direction normal to radiation beam 26, a flutter movement in the +Z and −Z directions occurs. Sheet flutter in the ±Z directions is caused by the geometries of moving material sheet 18 and may be induced by the velocity of material sheet 18, air currents, temperature and tensions on the sheet, etc. Such flutter movements can distort measurements of typical nuclear gauges.

Processor 20 communicates with detector array 16 by way of communications link 22. Information and/or signals from detector array 16 are received by processor 20 and such information or signals is processed to remove lateral misalignment between radiation source 12 and detector array 16 in an X and Y direction. Also, processor 20 determines the varying position of material sheet 18 in gap G. Processor 20 may be connected to other control aspects of nuclear gauge 10 and display and record data from the operation thereof. In addition, processor 20 calculates the basis weight of material sheet 18 and detects variations therein as material sheet 18 travels through nuclear gauge 10.

Radiation beam 26 is emitted from radiation source 12 through aperture 24 impacting material sheet 18 and at least some of the particles or radiation from radiation source 12 reaches detector array 16. Radiation beam 26 may be in the form of an energy and/or particle beam from radiation source 12 which travels in a substantially straight manner being somewhat directionally distorted by its encounter with material sheet 18. The amount of and manner of the distortion of radiation beam 26, as it interacts with material sheet 18, is dependent on many factors including the composition of material sheet 18, the relative thickness of material sheet 18, the Z positioning of material sheet 18 and the size of gap G.

Figure 4:
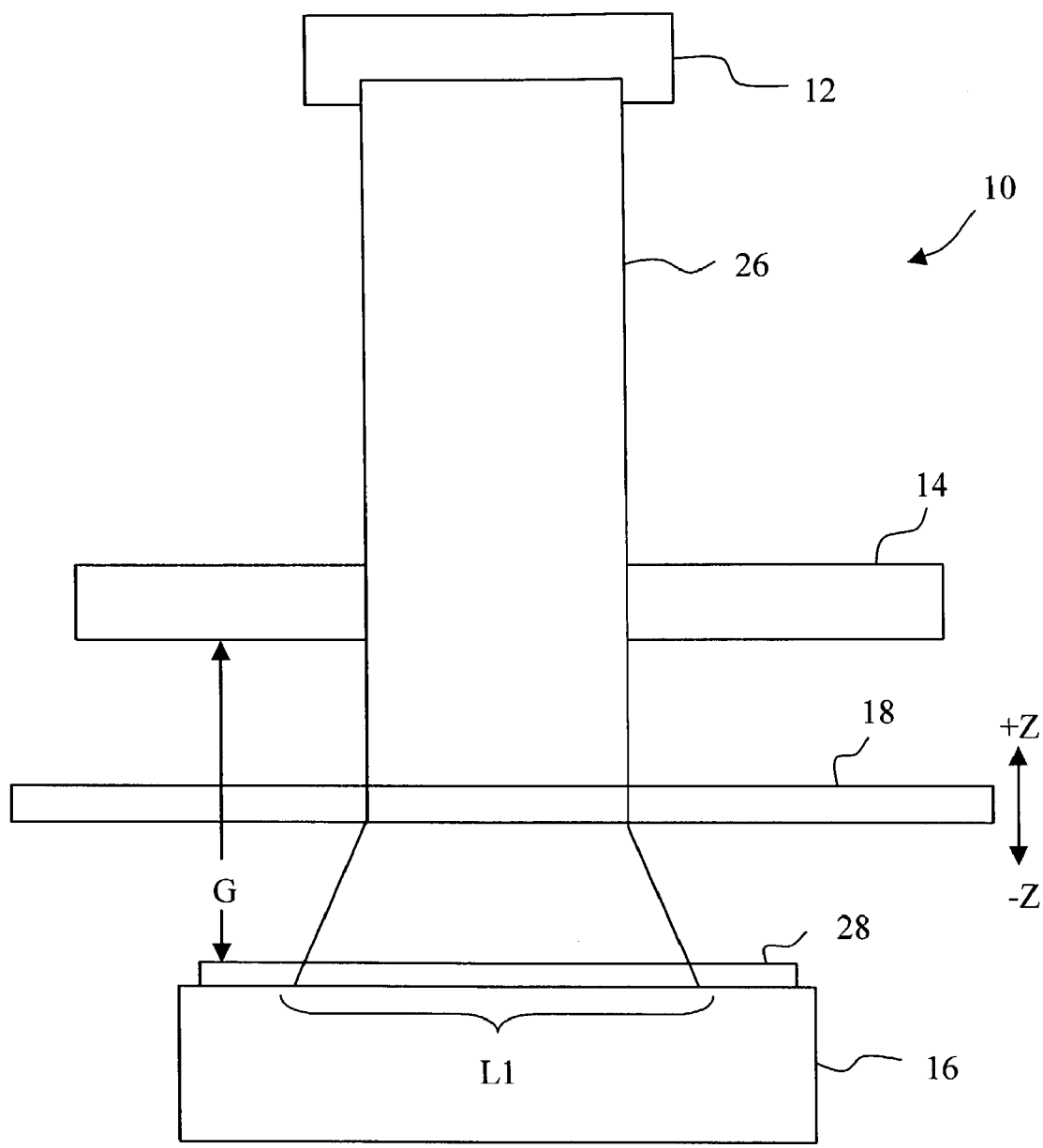
FIG. 4 is a diagrammatic side view of the nuclear gauge of FIG. 1 showing a radiation source at a distance from the aperture.
Figure 5:
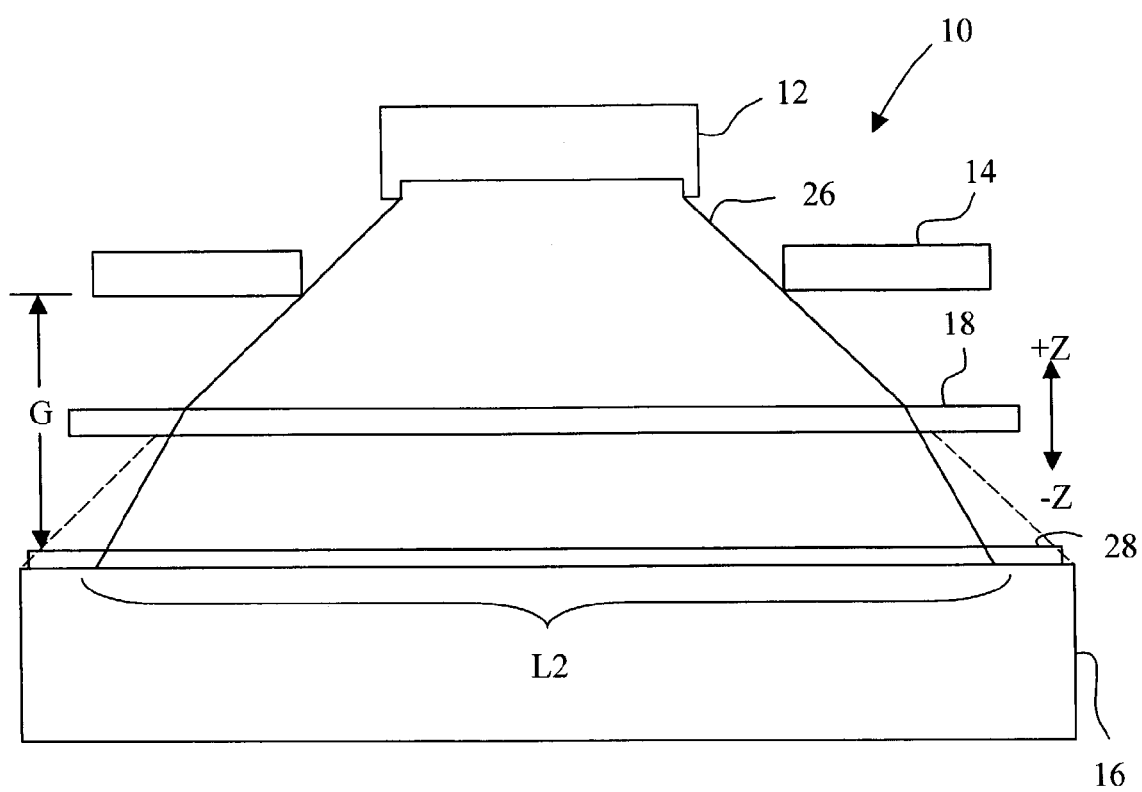
FIG. 5 is another diagrammatic side view of the present invention showing the radiation source closer to the aperture of the nuclear gauge of FIGS. 1 and 4.
Figure 6:
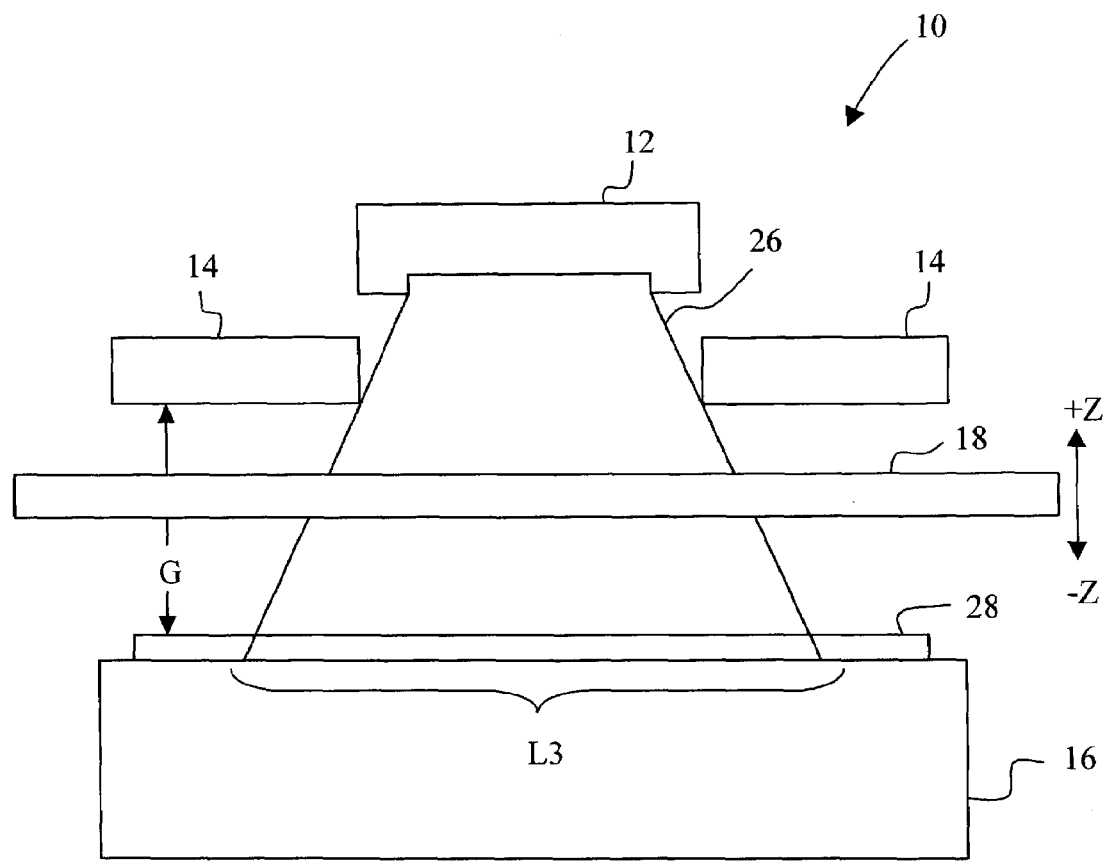
FIG. 6 is yet another diagrammatic side view of the nuclear gauge of FIGS. 1, 4 and 5.

Now additionally referring to FIGS. 4–6, there are shown variations in the location of radiation source 12 relative to source aperture 14. In FIG. 4 there is shown a relatively focused radiation beam 26 entering aperture 24, traveling in a non-distorted manner to material sheet 18, where radiation beam 26 is somewhat effected by material sheet 18 causing a dispersion of radiation beam 26 over a wider area, represented here by incident beam width L1. As can be deduced from FIG. 4, movement of material sheet 18 in a +Z direction will cause the spreading of radiation beam 26 thereby widening incident beam width L1. Conversely, when material sheet 18 moves in the −Z direction, incident beam width L1 decreases as its detected on detector array 16. Thus when material sheet 18 flutters the distribution of the radiation on detector array 16 varies, which causes incident beam width L1 to fluctuate.

Now referring to FIG. 5, there is shown radiation source 12 positioned relatively close to source aperture 14 and aperture 24 is wider than is shown in FIG. 4, thereby allowing a more angularly dispersed radiation beam 26 to interact on a wider area of material sheet 18. This sort of geometry causes a somewhat narrowing of the radiation beam after it goes through material sheet 18. Radiation beam 26, as it impacts detector array 16, is distributed over incident beam width L2, which is somewhat narrower than the angle at which radiation beam 26 passes through source aperture 14. As material sheet 18 moves or flutters in gap G, variations of incident beam width L2 occur, for example, as material sheet 18 moves in a +Z direction, incident beam width L2 decreases in size. Conversely, movement of material sheet 18 in the −Z direction causes incident beam width L2 to increase in dimension.

Now referring to FIG. 6, there is shown a compromise in the positioning of radiation source 12 and the size of aperture 24 so as to minimize the angular distortion of radiation beam 26 as it encounters material sheet 18, so that fluctuations in incident beam width L3 due to the variation in the position, in the ±Z direction, of material sheet 18 is reduced. However, the geometries of nuclear gauge 10, as shown in FIGS. 4–6, are all sensitive to the flutter of material sheet 18 and to variations in lateral alignment in the gap position. Even though FIG. 6 is a compromise that minimizes the effect of the flutter of material sheet 18, variations in the thickness and composition of material sheet 18 negatively effect the benefits of this compromise, in that such variations alter the deflection of radiation beam 26, thereby reducing the effectiveness of this sort of compromise.

Figure 8:
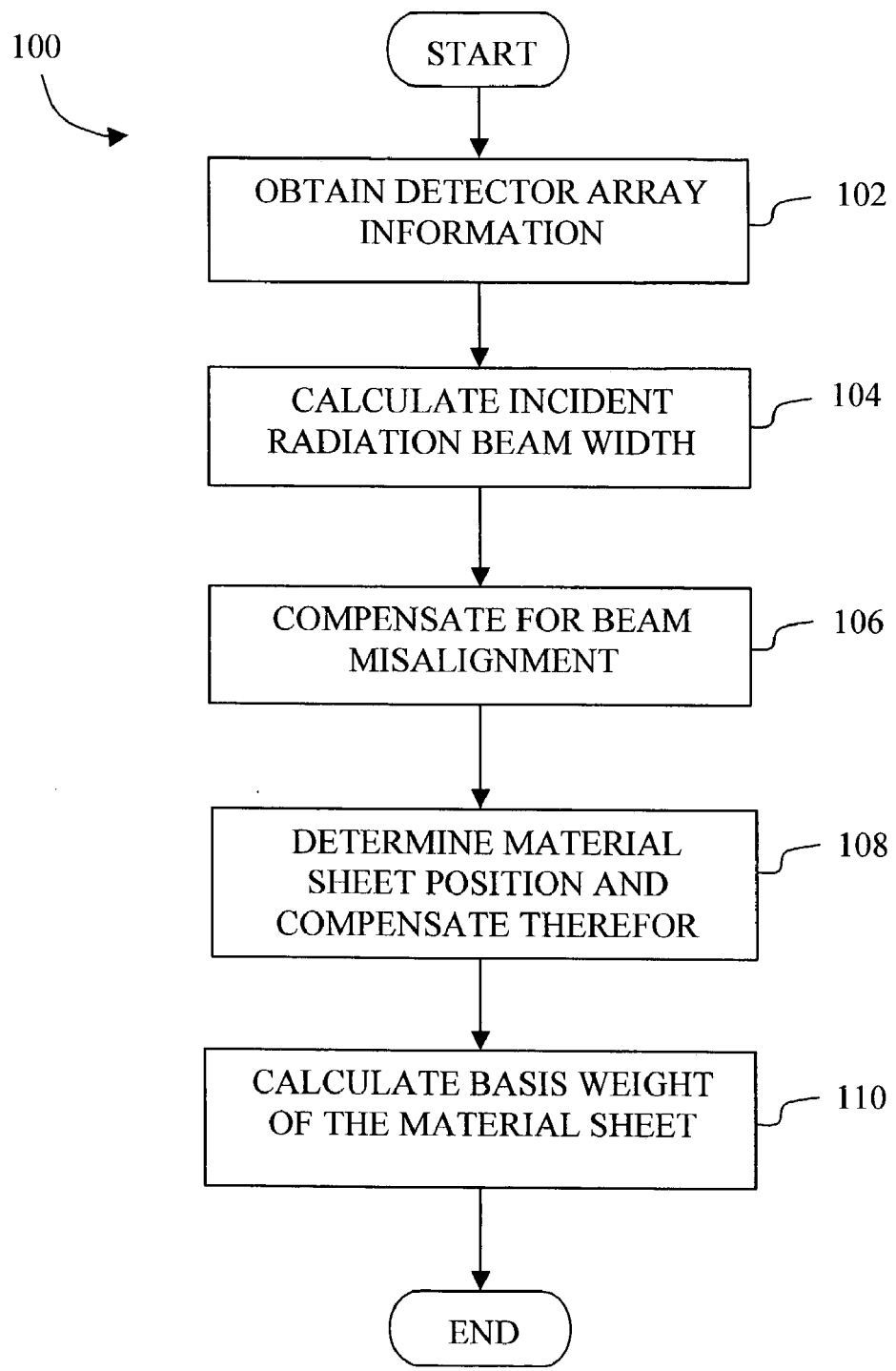
FIG. 8 is a block diagram of an embodiment of a method used by the nuclear gauge of FIGS. 1 and 2–6.

Now, additionally referring to FIG. 8, there is shown process 100 which is an embodiment of a method of the present invention. Including, obtaining detector array information at step 102. The radiation detected by each of sensors S11–S33 are individually transferred to processor 20 by way of communications link 22. This communications can take the form of a digital transmission of a count detected by each of sensors S11–S33 as a digitized representation of the amount of particles or energy falling on sensors S11–S33 or as analog signals from sensors S11–S33. The information or signals received by processor 20 are then individually quantized for each of sensors S11–S33.

At step 104, a calculation is done to determine the beam width of the incident radiation on detector array 16. The assumption is that the radiation from radiation source 12 is substantially centered on sensor S22 with the peak of the radiation intensity, as illustrated in FIG. 3, substantially directed to the center of sensor S22. The geometries of the sensors allow two calculations to be made of the relative strength of the radiation as it impacts sensors located farther from sensor S22. By utilizing the inputs from sensors S12, S21, S23 and S32 an effective detected radiation at a radius from S22 can be calculated. An additional calculation utilizing sensors S11, S13, S31 and S33 provide a second relative radiation intensity at another average radius from the presumed center of the radiation intensity. The number of and positioning geometry of the sensors allows multiple calculation to establish the intensity and distribution of the radiation incident on detector array 16. The beam shape or width is measured utilizing one or more ratios of signals from the detector as follows:

$$R1 = (S11+S13+S33+S31)/\{S22*[1+q1*(x^2+y^2)]\}$$

$$R2 = (S12+S23+S32+S21)/\{S22*[1+q2*(x^2+y^2)]\}$$

where: $x = (S23-S21)/(S23+S21)$
$y = (S12-S32)/(S12+S32)$
q1 and q2 are calibration constants
R1 is a first signal ratio representative of a first distance from the presumed center of radiation intensity
R2 is a second signal ratio representative of a second radius from the presumed center of radiation intensity.
x and y are utilized to compensate for lateral misalignments. In the event that there is no misalignment, x and y become zero in the equations.

The compensation for lateral misalignment at step 106 is accomplished by a portion of the denominator of the ratios R1 and R2, as shown above.

At step 108, the position of material sheet 18 is determined and compensated therefor. Both ratios R1 and R2 depend on the size of gap G and the effect that the sheet position has on radiation beam 26. If gap G is fixed or determined by a measurement, then the values of ratios R1 and R2 can be used to determine the position of material sheet 18 and to thereby compensate the signals from detector array 16 for the effects that the variations, in the position of material sheet 18, can inflect in the signals.

The values for ratios R1 and R2 also depend on the basis weight of material sheet 18. With very low basis weights the effect of material sheet 18 is small. With the increasing basis weight of material sheet 18 the beam shape, but not the overall intensity, will rapidly approach an asymptotic value becoming only slightly dependent on basis weight for higher values. For extremely high basis weights, with a beta radiation source, the beam shape appears to start becoming wider. This effect is caused by the high amount of bremsstrahlung x-rays that are emitted when most of the beta radiation is absorbed.

Figure 7:
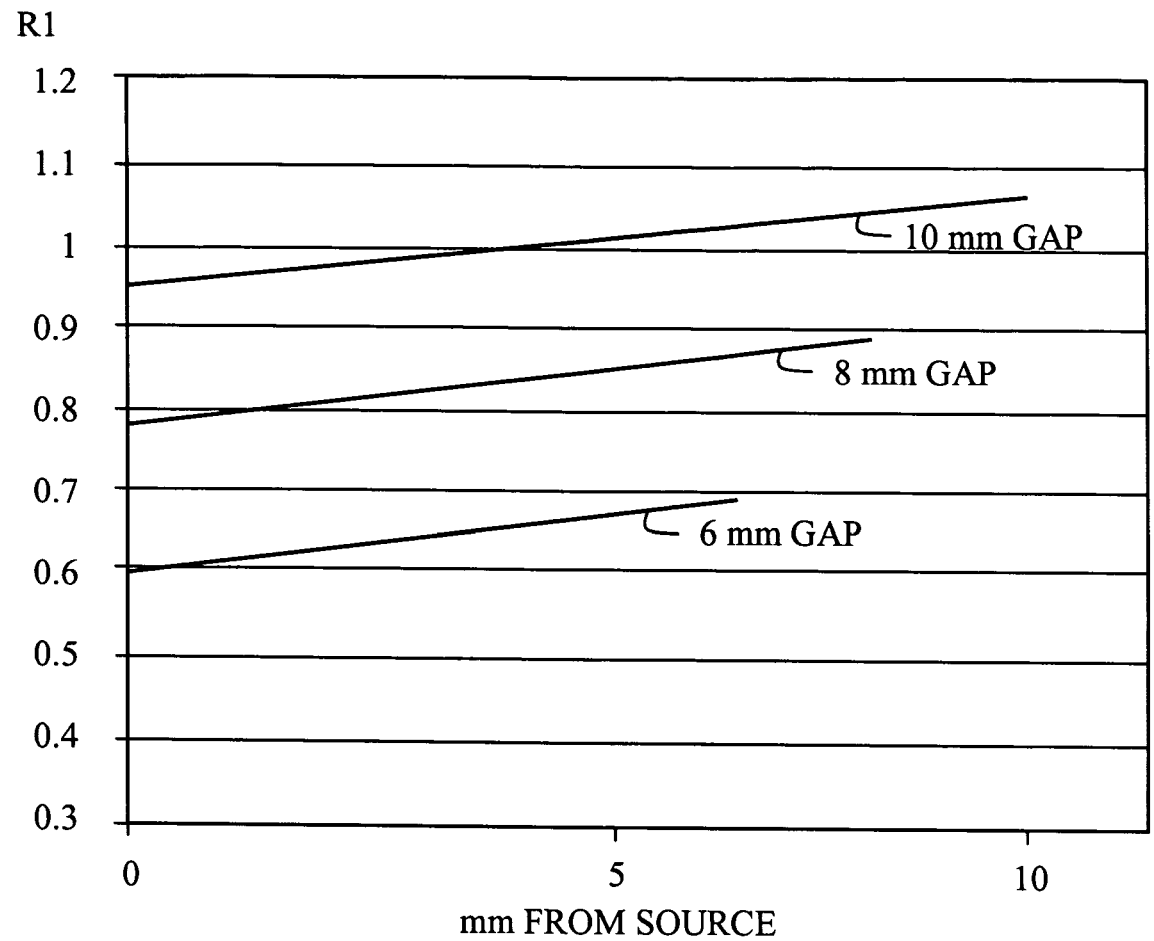
FIG. 7 is a graphical representation showing the result of a calculation of the position of the material sheet at various locations from the source based upon the gap between the source and the detector.

The dependence of ratio R1 on the size of gap G and the position of material sheet 18 in a Z direction, is illustrated in FIG. 7 wherein there is illustrated the effect of different gap sizes and the position of material sheet 18 relative to source aperture 14. With a fixed or known distance for gap G it can be seen that the present invention can determine the position of material sheet 18 between radiation source 12 and detector array 16.

The sheet position is calculated using the following algorithm:

$$\text{Position} = \{[(D*B)^T]*C\}$$

where:
D is a 4×4 matrix with calibration constants for sheet position and flutter compensation B is a 1×4 vector with the following elements:
1
(1−R0)
$(1-R0)^2$
$(1-R0)^3$ R0 is the sum of the signals from all detector elements divided by the value of that same sum with nothing in the measurement gap. R0 is used to make the position measurement independent of the basis weight of material sheet 18. In this case third power polynomials are used to do this correction, but other similar functions may be utilized.

The superscript T denotes a transposed matrix
C is a 1×4 vector with the following elements:
1
(R1/R10−1)
(R2/R20−1)
(Z−Z0)

Z is the measured gap size and Z0 is the nominal gap size at which the calibration constants were determined.
R10 and R20 are the nominal values for R1 and R2, R10 and R20 being empirically or computationally derived as a measurement of radiation without a material sheet 18 being between source 12 and detector 16.

At step 110, the basis weight of material sheet 18 is calculated. In summary the preferred algorithm, which will correct for errors caused in lateral x and y misalignment, gap size variations and sheet position variations, is as follows:

$$R = R0*\{1+[q3*(R1/R10)-q4*(R2/R20)^2]*(x^2+y^2)\}* \{[(A*B)^T]*C\}$$

where:
R is the signal that has been corrected for x and y misalignments and for material sheet 18 position variations in the Z direction.
Expression $\{1+[q3*(R1/R10)-q4*(R2/R20)^2]*(x^2+y^2)\}$ is the xy-correction algorithm. Constants q3 and q4 depend on sensor geometry and are determined during sensor calibration.
Term $\{[(A*B)^T]*C\}$ corrects for gap size and sheet position variations. This correction term is otherwise the same as the sheet position algorithm discussed above, except that calibration matrix A has a different set of elements. Vectors B and C are the same as those discussed above.

Finally, basis weight (BW) is calculated using the following formulas:

$$v = -1n(R)$$

$$BW = A+B*v+C*v^2+D*v^3$$

It can be understood that if radiation source 12 is from an x-ray source that essentially matrices A, C and D are equal to zero. Further, for the use of beta radiation, matrices A, C and D are needed to particularly compensate for variations in gap and paper position.

Figure 9:
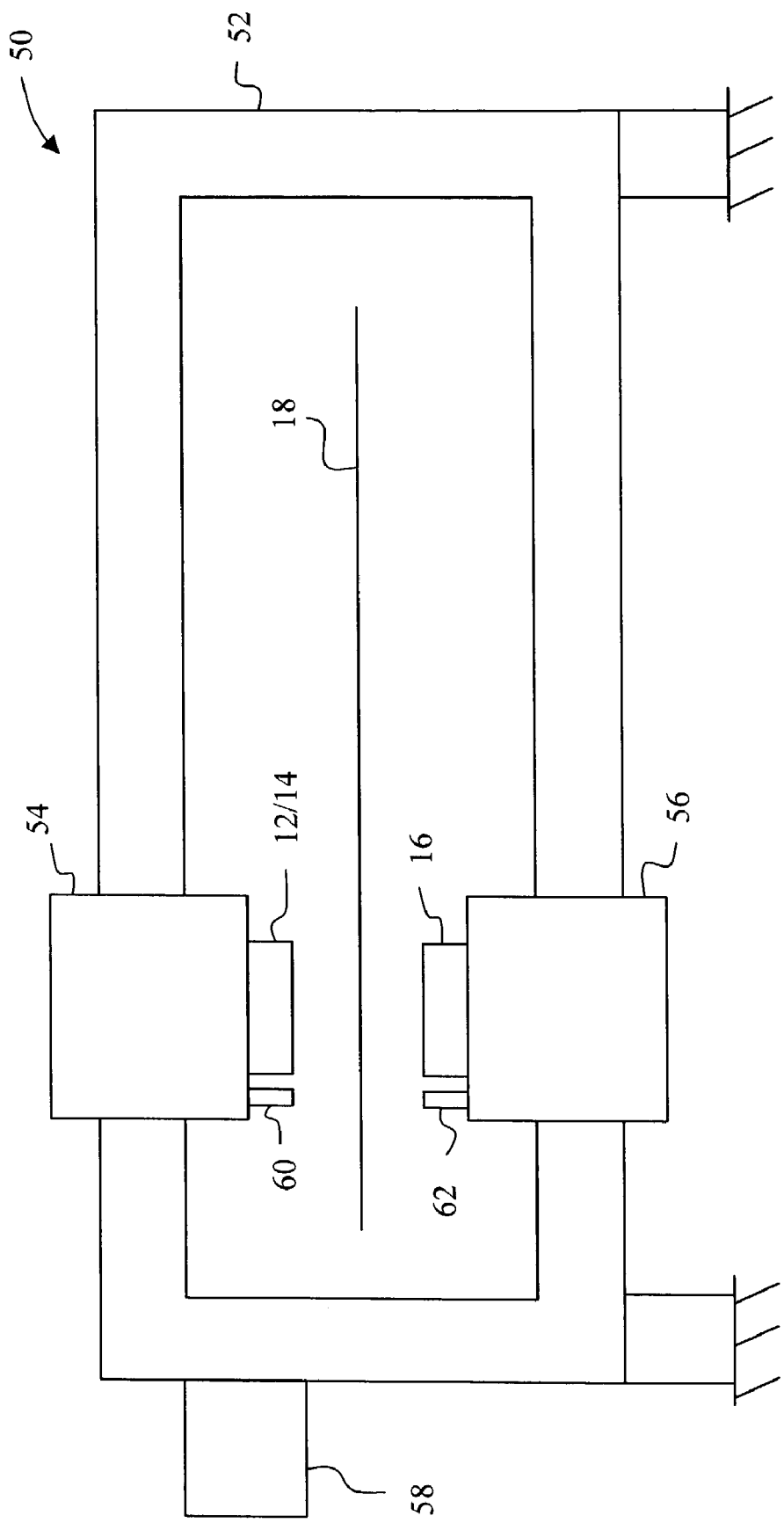
FIG. 9 is a diagrammatic side view of another embodiment of a nuclear gauge of the present invention.

Now, additionally referring to FIG. 9, there is shown a nuclear gauge 50 including a frame 52, a carriage 54, a carriage 56 and a drive mechanism 58. Drive mechanism 58 is interconnected to carriages 54 and 56 to move carriages 54 and 56 in a coordinated manner to keep radiation source 12 and source aperture 14 substantially aligned with detector array 16. Movements of carriages 54 and 56 are controlled in a bi-directional manner and are caused to move across material sheet 18 as material sheet 18 moves in a direction normal to FIG. 9. Nuclear gauge 50 thereby scans across the width of moving material sheet 18 obtaining information on a sampling basis as material sheet 18 moves through nuclear gauge 50. In addition, gap detection apparatus 60 and 62, also known as inductive devices 60 and 62, are positioned respectively on carriages 54 and 56. Inductive devices 60 and 62 are positioned to measure gap G and produce a gap signal which is proportional to the measured value. The gap signal is communicated to processor 20 thereby allowing processor 20 to utilize the aforementioned method to compensate for variations in gap G. Drive mechanism 58 moves carriages 54 and 56 along a substantial length of frame 52 along which there are unavoidable manufacturing variations, which induce some misalignment between radiation source 12 and detector array 16. These misalignments are compensated for by the present invention as described above. Alternatively, inductive devices 60 and 62 may be located directly on source aperture 14 and detector array 16 as shown in FIG. 1.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A material sheet attribute detection system, the material sheet having a first side and a second side, the system comprising:
   a radiation source located proximate to the first side of the material sheet, said radiation source emitting radiation toward the material sheet;
   a radiation detection array located proximate to the second side of the material sheet, said radiation detection array producing at least one signal based on said radiation detected from said radiation source; and
   a processor utilizing said at least one signal to determine a position of the material sheet.

2. The system of claim 1, wherein said processor additionally utilizes said at least one signal to determine a basis weight of the material sheet.

3. The system of claim 1, wherein said radiation emitted from said radiation source is in the form of a radiation beam, said processor utilizing said at least one signal to determine at least one beam width of said radiation beam.

4. The system of claim 3, wherein said processor additionally compensates for beam misalignment by utilizing said at least one beam width.

5. The system of claim 3, wherein said at least one beam width is determined after said radiation beam has passed through the material sheet.

6. The system of claim 1, further comprising a gap detector apparatus that produces a gap signal proportionate to the distance between said radiation source and said radiation detection array.

7. The system of claim 6, wherein said gap detection apparatus includes at least one inductive element.

8. The system of claim 6, wherein said processor additionally utilizes said gap signal to compensate for variations in the distance between said radiation source and said radiation detection array in the determination of said position of the material sheet.

9. The system of claim 1, wherein said radiation detection array includes a plurality of radiation sensors positioned in a predetermined pattern.

10. The system of claim 9, wherein said at least one signal is a plurality of signals, each of said plurality of radiation sensors producing a corresponding one of said plurality of signals.

11. The system of claim 1, wherein said processor utilizes said at least one signal to determine a basis weight of the material sheet, said processor also utilizing said at least one signal to compensate for said position of the material sheet and misalignment of said radiation source with said radiation detection array.

12. A material sheet attribute gauge, comprising:
   a transport mechanism including a first carriage and a second carriage, said first carriage and said second carriage being connected such that movement of said first carriage and said second carriage is coordinated to keep said first carriage and said second carriage in substantial alignment with each other;
   a radiation source positioned on said first carriage;
   a detector array positioned on said second carriage, said detector array producing information as to the amount of radiation received from said radiation source; and
   a processor that utilizes said information to determine a position of the material sheet between said radiation source and said detector array.

13. The system of claim 12, wherein said processor additionally utilizes said information to determine a basis weight of the material sheet.

14. The system of claim 12, wherein said radiation source emits radiation therefrom in the form of a radiation beam, said processor utilizing said information to determine at least one beam width of said radiation beam.

15. The system of claim 14, wherein said processor additionally compensates for beam misalignment by utilizing said at least one beam width.

16. The system of claim 14, wherein said at least one beam width is determined after said radiation beam has passed through the material sheet.

17. The system of claim 14, further comprising a gap detector apparatus that produces a gap signal proportionate to the distance between said radiation source and said detector array.

18. The system of claim 17, wherein said gap detection apparatus includes an inductive element.

19. The system of claim 17, wherein said processor additionally utilizes said gap signal to compensate for variations in the distance between said radiation source and said detector array in the determination of said position of the material sheet.

20. The system of claim 12, wherein said detector array includes a plurality of radiation sensors positioned in a predetermined pattern.

21. The system of claim 20, wherein said information includes data from said plurality of radiation sensors.

22. The system of claim 12, wherein said processor utilizes said information to determine a basis weight of the material sheet, said processor also utilizing said information to compensate for said position of the material sheet and misalignment of said radiation source with said detector array.

23. A method of measuring attributes of a moving material sheet, comprising the steps of:

positioning a radiation source on one side of the material sheet and a detector array on an other side of the material sheet;

receiving information from said detector array; and calculating a position of the material sheet between said radiation source and said detector array using said information.

24. The method of claim 23, further comprising the step of calculating a basis weight of the material sheet using said information.

25. The method of claim 23, further comprising the step of calculating at least one beam width incident on said detector array using said information.

26. The method of claim 25, further comprising the step of compensating for a beam misalignment based on said calculating step of said at least one beam width.

27. The method of claim 23, further comprising the steps of:

determining a gap distance from said radiation source to said detector array;

utilizing said gap distance in said calculating step to compensate for variations in said gap distance.

28. The method of claim 27, further comprising the step of compensating for changes in said position of the material sheet and utilizing said gap distance in a calculation of the basis weight of the material.

29. The method of claim 28, wherein said compensating step also compensates for lateral misalignment of said radiation source with said detector array.

* * * * *